(12) United States Patent
Zimmer et al.

(10) Patent No.: US 7,008,799 B1
(45) Date of Patent: *Mar. 7, 2006

(54) ANALYTICAL TEST ELEMENT WITH A CAPILLARY CHANNEL

(75) Inventors: Volker Zimmer, Dossenheim (DE); Wolfgang Schwöbel, Mannheim (DE); Ronald Mönch, Mannheim (DE); Wilhelm Leichner, Mannheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/554,844

(22) PCT Filed: Dec. 4, 1998

(86) PCT No.: PCT/EP98/07886

§ 371 (c)(1),
(2), (4) Date: Sep. 19, 2000

(87) PCT Pub. No.: WO99/29429

PCT Pub. Date: Jun. 17, 1999

(30) Foreign Application Priority Data

Dec. 4, 1997 (DE) ................................. 197 53 847

(51) Int. Cl.
*G01N 33/558* (2006.01)

(52) U.S. Cl. .................. 436/514; 422/68.1; 422/82.05; 422/82.09; 422/82.11; 435/287.1; 435/287.2; 435/287.7; 435/287.8; 435/287.9; 435/288.5; 435/288.7; 435/808; 436/164; 436/172; 436/518; 436/524; 436/532; 436/807

(58) Field of Classification Search .................. 435/4, 435/6, 7.1, 7.9, 7.92, 287.1–287.3, 287.7–287.9, 435/288.5, 288.7, 808, 969; 436/164, 172, 436/518, 524, 532, 807, 514; 422/68.1, 82.05, 422/82.09, 82.11
See application file for complete search history.

(56) References Cited

U.S. PATENT DOCUMENTS 3,715,192 A * 2/1973 Wenz et al. .................. 422/56

(Continued)

FOREIGN PATENT DOCUMENTS

DE 196 29 656 A1 1/1998

(Continued)

*Primary Examiner*—Christopher L. Chin
(74) *Attorney, Agent, or Firm*—Jill Woodburn; Sujatha Subramaniam; Justin Sage

(57) ABSTRACT

The invention concerns an analytical test element for the determination of an analyte in a liquid containing an inert carrier, a detection element and a channel capable of capillary liquid transport which has a sample application opening at one end and a vent opening at the other end of the channel capable of capillary liquid transport, wherein the channel capable of capillary liquid transport is formed at least partially by the carrier and the detection element and extends in the direction of capillary transport from the sample application opening at least to the edge of the detection test element that is nearest to the vent opening and wherein a notch is located in one of the surfaces forming the channel capable of capillary liquid transport at the edge of the test element forming the sample application opening so that one side of the edge of the test element forming the sample application opening is at least partially discontinuous and the surface opposite to the notch is exposed. It also concerns the use of the said analytical test element for the determination of an analyte in a liquid as well as a method for the determination of an analyte in a liquid sample with the aid of the said analytical test element.

32 Claims, 6 Drawing Sheets

U.S. PATENT DOCUMENTS

| | | | |
|---|---|---|---|
| 4,138,216 A | 2/1979 | Larsson et al. | 422/58 |
| 4,250,257 A | 2/1981 | Lee et al. | 435/4 |
| 4,254,083 A | 3/1981 | Columbus | 422/55 |
| 4,312,834 A | 1/1982 | Vogel et al. | 422/56 |
| 4,323,536 A | 4/1982 | Columbus | 422/56 |
| 4,354,308 A | 10/1982 | Shimada et al. | 438/49 |
| 4,439,526 A | 3/1984 | Columbus | 436/180 |
| 4,588,624 A | 5/1986 | Nygren et al. | 428/36 |
| 4,826,772 A | 5/1989 | Meathrel | 436/93 |
| 4,900,663 A | 2/1990 | Wie et al. | 435/7.32 |
| 4,933,092 A | 6/1990 | Aunet et al. | 210/729 |
| 4,952,373 A | 8/1990 | Sugarman et al. | 422/99 |
| 5,006,474 A | 4/1991 | Horstman et al. | 436/524 |
| 5,071,746 A | 12/1991 | Wilk et al. | 435/7.94 |
| 5,100,627 A | 3/1992 | Buicn et al. | 422/108 |
| 5,147,606 A | 9/1992 | Charlton et al. | 422/56 |
| 5,173,433 A | 12/1992 | Bachand | 436/169 |
| 5,192,502 A | 3/1993 | Attridge et al. | 422/57 |
| 5,208,163 A | 5/1993 | Charlton et al. | 436/63 |
| 5,264,103 A | 11/1993 | Yoshioka et al. | 205/778 |
| 5,271,895 A | 12/1993 | McCroskey et al. | 422/58 |
| 5,310,525 A | 5/1994 | Churchouse et al. | 422/56 |
| 5,395,504 A | 3/1995 | Saurer et al. | 204/403.03 |
| 5,395,506 A | 3/1995 | Duce et al. | 204/426 |
| 5,399,316 A | 3/1995 | Yamada | 422/58 |
| 5,405,511 A | 4/1995 | White et al. | 205/777.5 |
| 5,437,999 A | 8/1995 | Diebold et al. | 204/403.11 |
| 5,575,895 A | 11/1996 | Ikeda et al. | 204/403.1 |
| 5,714,123 A | 2/1998 | Sohrab | 422/99 |
| 5,741,634 A | 4/1998 | Nozoe et al. | 204/403.03 |
| 5,759,364 A | 6/1998 | Charlton et al. | 204/403.14 |
| 5,762,770 A | 6/1998 | Pritchard et al. | 204/403.14 |
| 5,814,522 A * | 9/1998 | Zimmer et al. | 436/170 |
| 5,843,691 A | 12/1998 | Douglas et al. | 435/14 |
| 5,846,837 A * | 12/1998 | Thym et al. | 436/170 |
| 5,851,838 A * | 12/1998 | Vetter et al. | 436/170 |
| 5,942,102 A | 8/1999 | Hodges et al. | 205/775 |
| 5,962,215 A | 10/1999 | Douglas et al. | 435/4 |
| 5,997,817 A * | 12/1999 | Crismore et al. | 204/403.1 |
| 6,025,203 A * | 2/2000 | Vetter et al. | 436/170 |
| 6,036,919 A | 3/2000 | Thym et al. | 422/58 |
| 6,174,420 B1 | 1/2001 | Hodges et al. | 204/403 |
| 6,238,624 B1 | 5/2001 | Heller et al. | 422/68.1 |
| 6,325,975 B1 | 12/2001 | Naka et al. | 422/61 |
| 6,592,815 B1 * | 7/2003 | Zimmer | 422/58 |

FOREIGN PATENT DOCUMENTS

| | | |
|---|---|---|
| EP | 0 010 456 A1 | 4/1980 |
| EP | 0 016 387 B1 | 10/1980 |
| EP | 0 034 049 B1 | 8/1981 |
| EP | 0 045 476 A1 | 2/1982 |
| EP | 0 138 152 B1 | 4/1985 |
| EP | 0 287 883 A1 | 10/1988 |
| EP | 0 330 517 A2 | 8/1989 |
| EP | 0 852 336 A1 | 7/1998 |
| GB | 2090659 A | 7/1982 |
| WO | WO 94/22011 | 9/1994 |
| WO | WO 96/28715 | 9/1996 |
| WO | WO 97/18465 | 5/1997 |
| WO | WO 98/22625 | 5/1998 |

* cited by examiner

FIG. 1
FIG. 1A
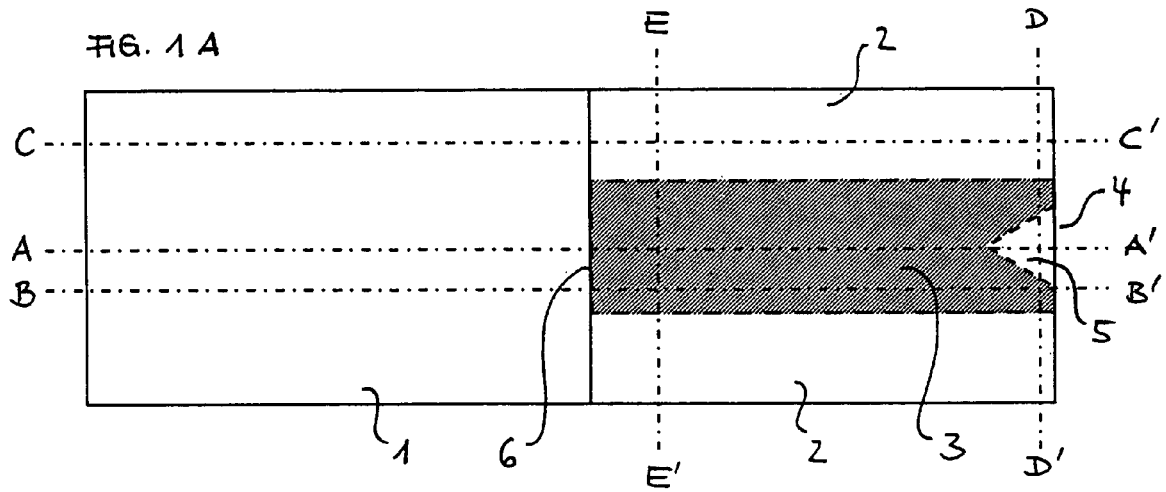
FIG. 1B
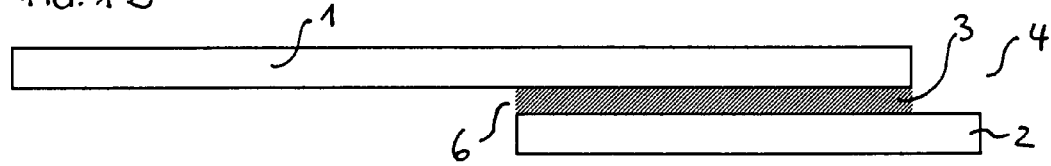
FIG. 1C
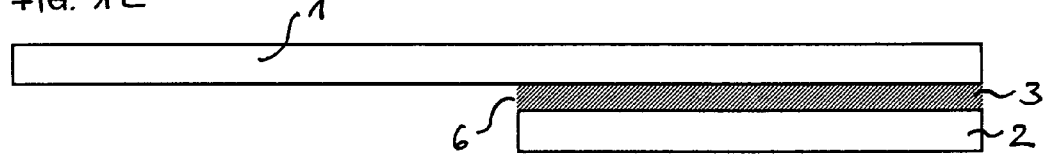
FIG. 1D
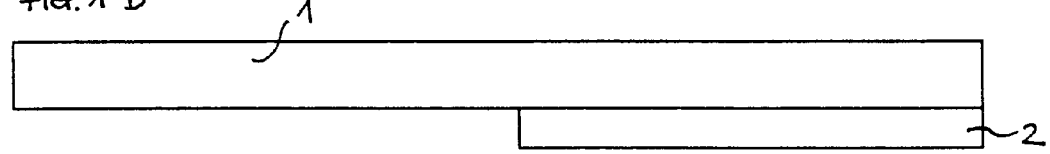
FIG. 1E
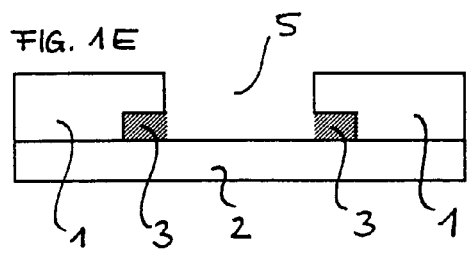
FIG. 1F
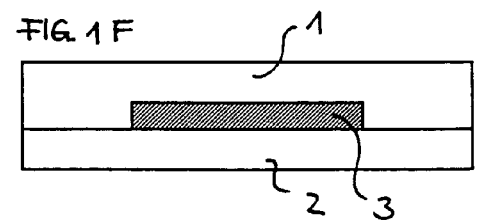

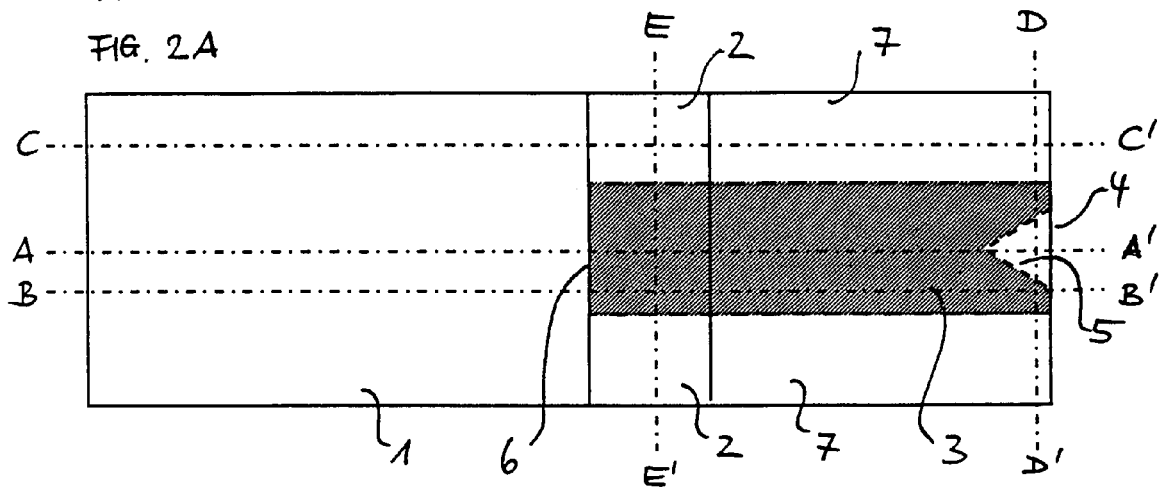
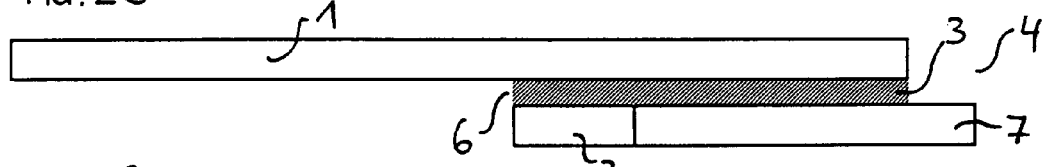
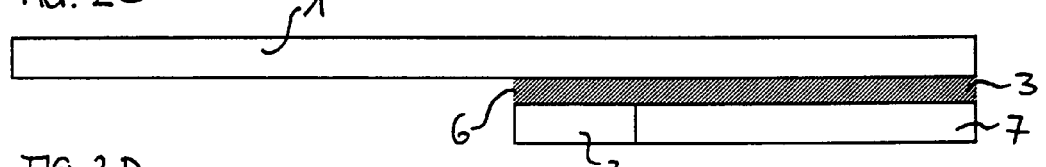
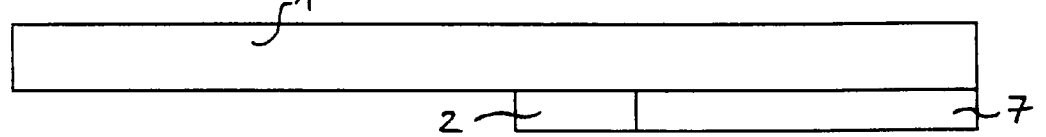
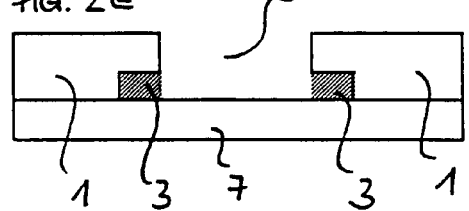
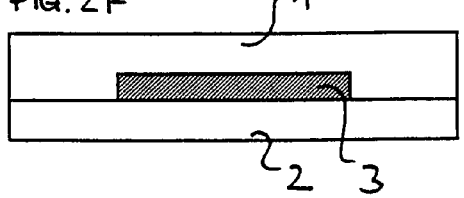

FIG. 3
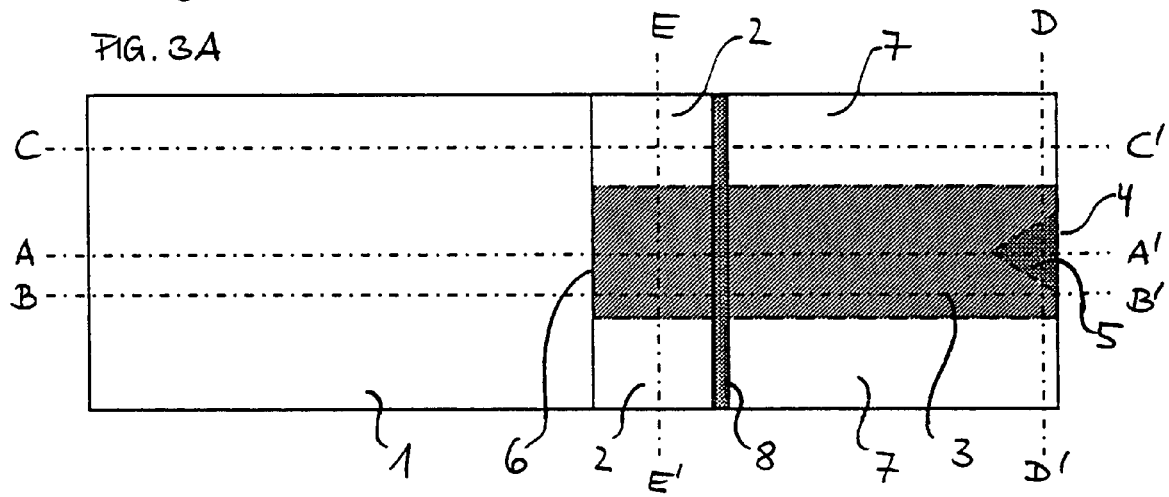
FIG. 3A
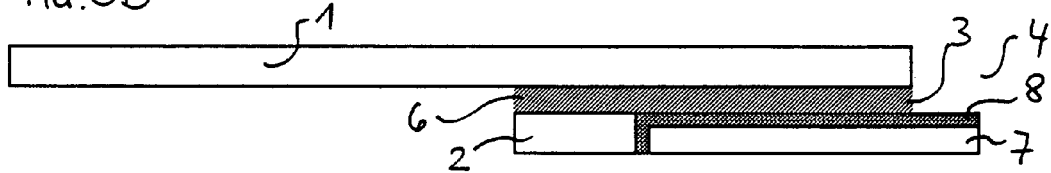
FIG. 3B
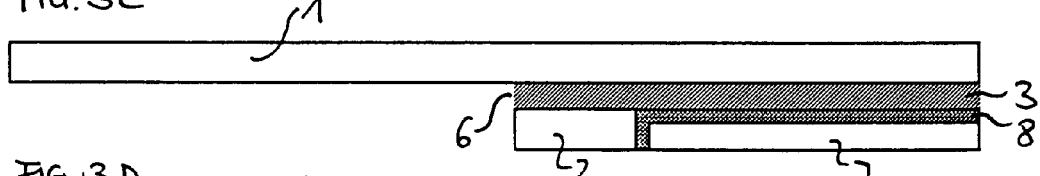
FIG. 3C
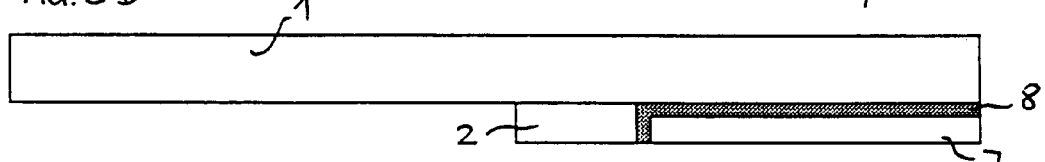
FIG. 3D
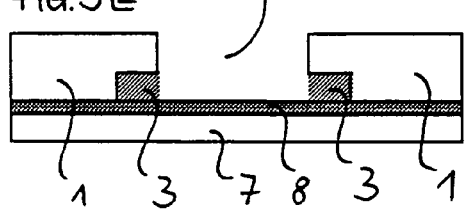
FIG. 3E
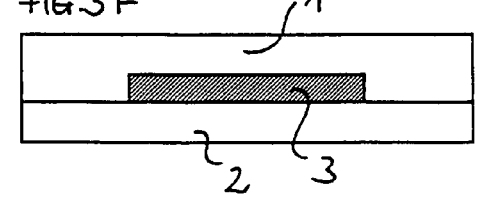
FIG. 3F FIG. 4
FIG. 4A
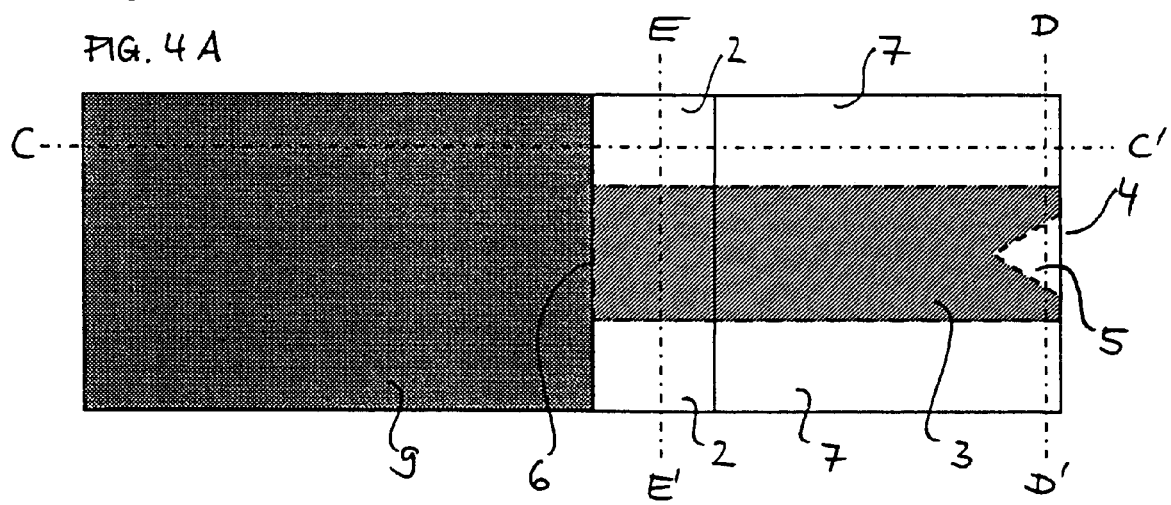
FIG. 4B
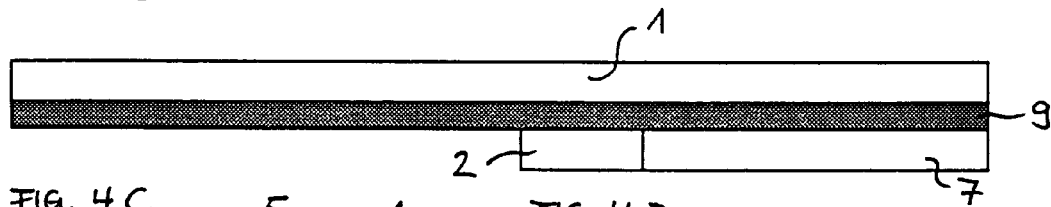
FIG. 4C
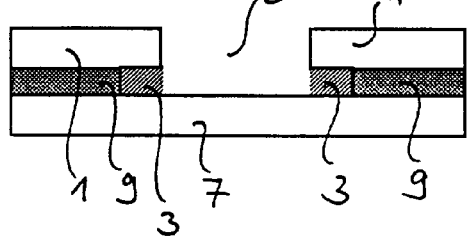
FIG. 4D
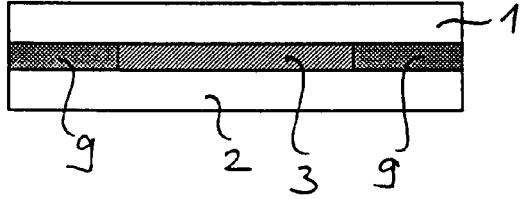

FIG. 5
FIG. 5A
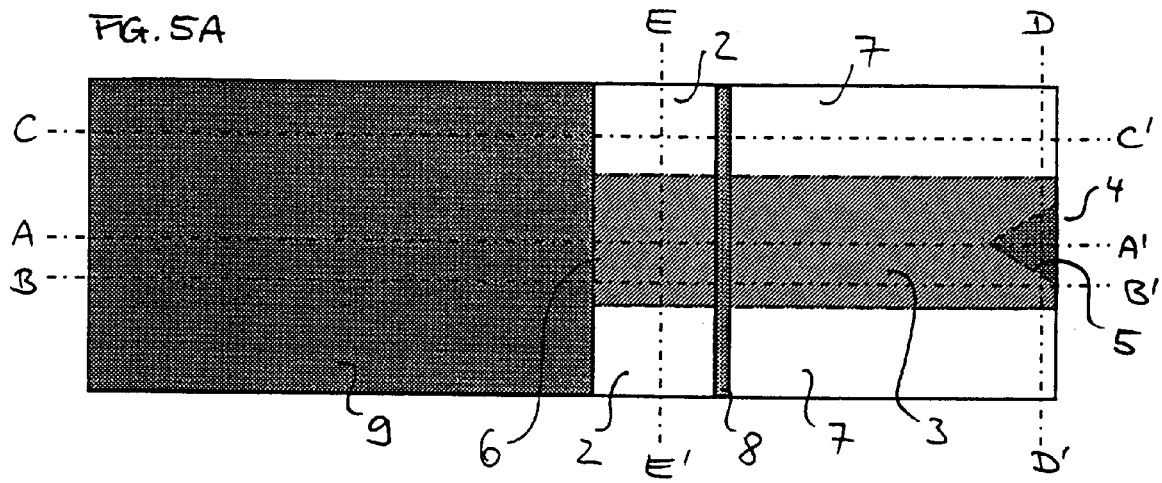
FIG. 5B
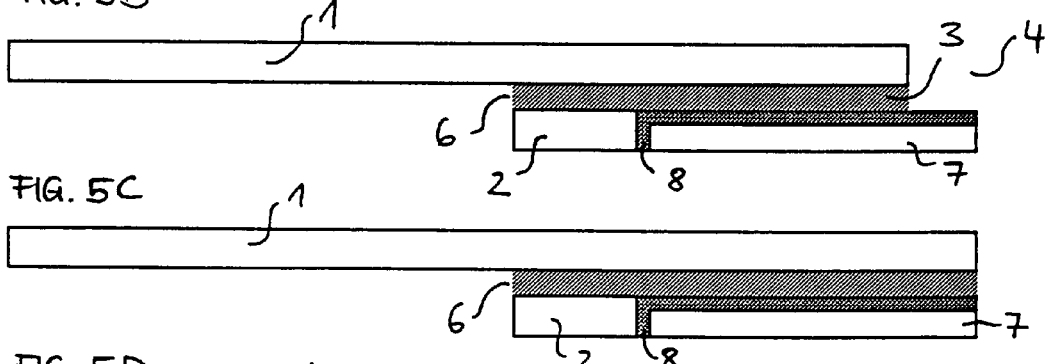
FIG. 5C
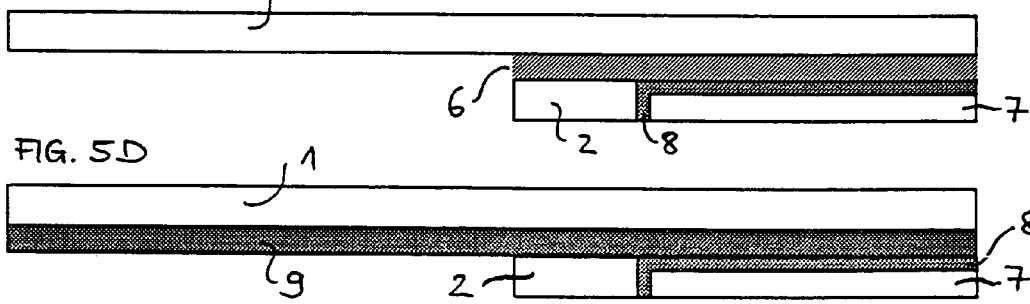
FIG. 5D
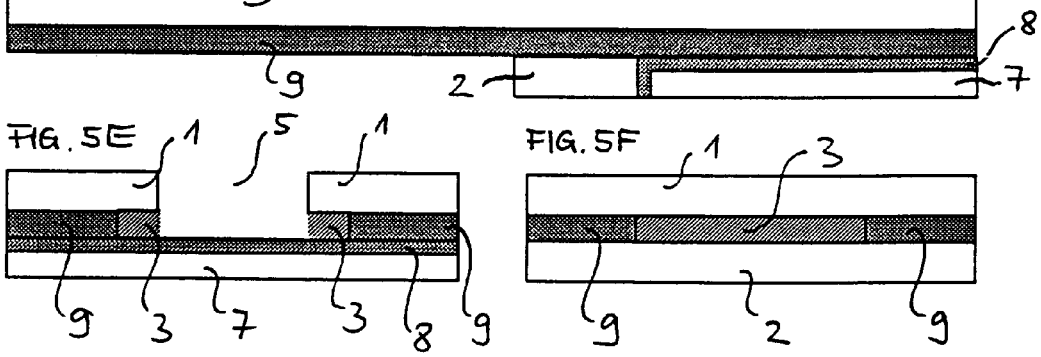
FIG. 5E 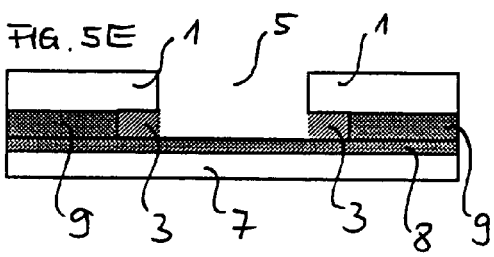 FIG. 5F 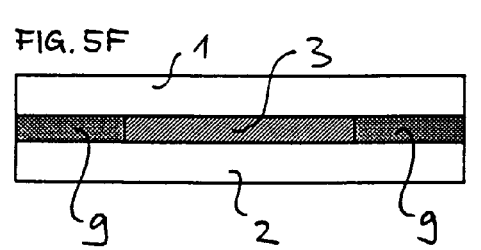
FIG. 5G
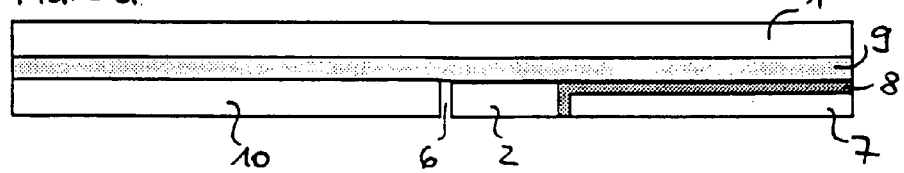

ANALYTICAL TEST ELEMENT WITH A CAPILLARY CHANNEL

CROSS-REFERENCE TO RELATED APPLICATION

The present application is a 371 of PCT/EP98/07886 filed Dec. 4, 1998, and claims priority to German application serial no. 197 53 847.9, filed Dec. 4, 1997.

BACKGROUND AND SUMMARY OF THE INVENTION

The invention concerns an analytical test element for the determination of an analyte in a liquid containing an inert carrier, a detection element and a channel capable of capillary liquid transport, which has a sample application opening at one end and a vent opening at the other end of the channel capable of capillary liquid transport. The invention also concerns the use of the said analytical test element for the determination of an analyte in a liquid as well as a method for the determination of an analyte in a liquid sample with the aid of the said analytical test element.

So-called carrier-bound tests are often used for the qualitative or quantitative analytical determination of components of body fluids, in particular of blood. In these the reagents are embedded in corresponding layers of a solid carrier which is contacted with the sample. If a target analyte is present, the reaction of the liquid sample and reagents leads to a detectable signal, in particular a colour change which can be evaluated visually or with the aid of an instrument, usually by reflection photometry.

Test elements or test carriers are often in the form of test strips which are essentially composed of an elongate carrier layer made of plastic material and detection layers which are applied thereto as test fields. However, test carriers are also known which are in the shape of small quadratic or rectangular plates.

Test elements for clinical diagnostics that are evaluated visually or by reflection photometry are frequently constructed such that the sample application zone and the detection zone are arranged one above the other in a vertical axis. This mode of construction is problematic. When the test strip loaded with sample has to be inserted into an instrument, for example a reflection photometer, for measurement, potentially infectious sample material can come into contact with parts of the instrument and may contaminate them. Furthermore volumetric dosing can only be achieved with difficulty especially in cases in which the test strips are used by untrained persons for example in the self-control of blood sugar by diabetics. Moreover conventional test elements often require relatively large sample volumes due to their construction in order to enable reliable measurements. The more sample volume is required, the more painful this can be for the patient whose blood is to be examined. It is therefore a general goal to provide test strips which require as little sample material as possible.

EP-B 0 138 152 deals with a disposable cuvette which is suitable for almost simultaneously taking up sample liquid into a sample chamber with the aid of a capillary gap and measuring. Reagents for specific detection reactions can be provided in the inside of the capillary cavity. The cavity is at least partially bounded by a semipermeable membrane. The reagents can for example be attached by coating the walls or by embedding the reagents in a semipermeable membrane in the cavity.

EP-A-0 287 883 describes a test element which utilizes a capillary interspace between the detection layer and an inert carrier for volumetric dosing. The test element is dipped into the sample to be examined to fill the capillary space which requires large sample volumes which is why this type of volumetric dosing is primarily suitable for the examination of sample material that is present in excess such as urine. There is no spatial separation between the site of sample application and detection.

EP-B-0 034 049 concerns a test element in which the sample is applied to a central sample application site for example an opening in a cover and is transported by capillary force to several detection zones which are spatially separated from the sample application site. The central position of the sample application site in a test element according to EP-B-0 034 049 does not solve the problem of instrument hygiene as described above.

The object of the present invention was to eliminate the disadvantages of the prior art. In particular it was intended to provide a simple to handle test element that can automatically dose volumes and enable a spatial separation of the detection zone and sample application site while using minimal sample volumes. In addition the sample transport from sample application to the detection zone should be so rapid that this does not limit the time required to analyse a sample. Furthermore a simple construction of the test element should enable the test element to be manufactured cost-effectively and simply.

This is achieved by the subject matter of the invention as characterized in the patent claims.

The subject matter of the invention is an analytical test element for the determination of an analyte in a liquid containing an inert carrier, a detection element and a channel capable of capillary liquid transport which has a sample application opening at one end and a vent opening at the other end of the channel capable of capillary liquid transport characterized in that the channel capable of capillary liquid transport is formed at least partially by the carrier and the detection element and extends in the direction of capillary transport from the sample application opening to at least the edge of the detection element that is nearest to the vent opening and that a notch is located in one of the surfaces forming the channel capable of capillary liquid transport at the edge of the test element forming the sample application opening so that one side of the edge of the test element forming the sample application opening is at least partially discontinuous and the surface opposite to the notch is exposed.

Since the channel capable of capillary liquid transport completely spans the detection element in the direction of capillary transport, this ensures that inhomogeneous wetting of the detection element with sample is avoided. In particular the layer thickness of the sample liquid that is in contact with the detection element is reproducibly pre-determined by the height of the capillary-active channel over the entire area of the detection element that covers the capillary-active channel. This enables a substantially uniform spatially distributed detection reaction. This therefore increases the precision and reproducibility of the measurement.

Since, in the preferred case that the channel has an essentially rectangular cross-section, one dimension, for example the height of the channel, is preset by the physical limits of capillary activity, the volume of the capillary channel can be adjusted by suitable selection of the two other dimensions for example length and width. The height of the capillary is for example for aqueous liquids of the order of magnitude of 10 to 500 $\mu$m, preferably between 20 and 300 μm and especially preferably between 50 and 200 μm, since otherwise no capillary activity is observed. Depending on the desired volume the width can then be several mm preferably 1 to 10 mm, most preferably 1 to 3 mm and the length can be up to several cm, preferably 0.5 to 5 cm and especially preferably 1 to 3 cm.

The notch in a surface forming the capillary channel at the edge of the test element which forms the sample application opening serves to ensure that the sample liquid can enter the capillary channel. This is achieved in that the sample drop can be directly contacted with one of the surfaces, whose extension forms the inner surface of the capillary, at the edge of the test element that is broken by the notch which is nearest the sample application opening. Suitable selection of the geometry and dimensions of the notch ensures that the liquid drop comes into contact with the capillary active zone with very high probability, independent of the exact position of the dosing and is readily sucked into the inside of the capillary. For example the size of the exposed surface should be selected such that at least one site of the liquid drop that is applied thereto comes into contact with the capillary active zone. For example one dimension of the notch for example its width should be selected such that the diameter of the liquid drop is slightly larger than the selected dimension of the notch. A notch width of 1 mm has proven to be suitable for a drop of 3 μl. Suction of the sample drop into the capillary channel is particularly preferably achieved by the area exposed by the notch being hydrophilized and bordering directly on a capillary active zone at least in the direction of the capillary transport channel.

In this connection hydrophilic surfaces are water-attracting surfaces. Aqueous samples, also including blood, spread well on such surfaces. Such surfaces are characterized among others in that a water drop placed on it forms an acute rim angle or contact angle at the interface. In contrast an obtuse rim angle is formed at the interface between the water drop and the surface on hydrophobic i.e. water repellent surfaces.

The rim angle which is a result of the surface tensions of the test liquid and of the surface to be examined is a measure of the hydrophilicity of a surface. Water for example has a surface tension of 72 mN/m. If the value of the surface tension of the observed surface is much below this value i.e. more than 20 mN/m, then the wetting is poor and the resulting rim angle is obtuse. Such a surface is referred to as hydrophobic. If the surface tension approximates the value which is found for water then the wetting is good and the rim angle is acute. If, in contrast, the surface tension is the same as or higher than that of the value found for water, then the drop runs and there is a total spreading of the liquid. It is then no longer possible to measure a rim angle. Surfaces which form an acute rim angle with water drops or on which a total spreading of a water drop is observed are referred to as hydrophilic.

The ability of a capillary to suck up a liquid depends on the wettability of the channel surface with the liquid. This means for aqueous samples that a capillary should be manufactured from a material whose surface tension almost reaches 72 mN/m or exceeds this value.

Sufficiently hydrophilic materials for the construction of a capillary which rapidly sucks up aqueous samples are for example glass, metal or ceramics. However, these materials are unsuitable for use in test carriers since they have some severe disadvantages such as risk of breaking in the case of glass or ceramics or change in the surface properties with time in the case of numerous metals. Therefore plastic foils or moulded parts are usually used to manufacture test elements. As a rule the plastics used hardly exceed a surface tension of 45 mN/m. Even with the, in a relative sense, most hydrophilic plastics such as polymethylmethacrylate (PMMA) or polyamide (PA) it is only possible—if at all—to construct slowly sucking capillaries. Capillaries made of hydrophobic plastics such as for example polystyrene (PS), polypropylene (PP) or polyethylene (PE) essentially do not suck aqueous samples. Consequently it is necessary to endow the plastics used as a construction material for test elements with capillary active channels with hydrophilic properties i.e. to hydrophilize them.

In a preferred embodiment of the analytical test element according to the invention at least one, but preferably two and especially preferably two opposite surfaces which form the inner surface of the channel capable of capillary liquid transport are hydrophilized. At least the exposed surface opposite the notch is very preferably hydrophilized. If more than one surface is hydrophilized then the surfaces can either be made hydrophilic using the same or different methods. Hydrophilization is particularly necessary when the materials that form the capillary active channel, in particular the carrier, are themselves hydrophobic or only very slightly hydrophilic because they are for example composed of nonpolar plastics. Nonpolar plastics such as for example polystyrene (PS), polyethylene (PE), polyethylene terephthalate (PET) or polyvinyl chloride (PVC) are advantageous as carrier materials because they do not absorb the liquids to be examined and thus the sample volume can be effectively utilized by the detection layer. The hydrophilization of the surface of the capillary channel enables a polar, preferably aqueous, sample liquid to readily enter the capillary channel and be rapidly transported there to the detection element or to the site of the detection element where the detection takes place.

Ideally the hydrophilizaton of the surface of the capillary channel is achieved by using a hydrophilic material in its manufacture which, however, cannot itself suck up the sample liquid or only to a negligible extent. In cases where this is not possible a hydrophobic or only very slightly hydrophilic surface can be hydrophilized by suitable coating with a stable hydrophilic layer that is inert towards the sample material for example by covalently binding photoreactive hydrophilic polymers onto a plastic surface by applying layers containing wetting agents or by coating surfaces with nanocomposites by means of sol-gel technology. Furthermore it is also possible to achieve an increased hydrophilicity by thermal, physical or chemical treatment of the surface.

The hydrophilization is quite especially preferably achieved by using thin layers of oxidized aluminium. These layers are either applied directly to the desired components of the test element for example by vacuum metallizing the work pieces with metallic aluminium and subsequently oxidizing the metal, or by using metal foils or metal-coated plastics for the construction of the test carriers which also have to be oxidized to achieve the desired hydrophilicity. In this case metal layer thicknesses of 1 to 500 nm are adequate. The metal layer is subsequently oxidized to form the oxidized form in which case above all oxidation in the presence of water vapour or by boiling in water have proven to be especially suitable methods in addition to electrochemical, anodic oxidation. The oxide layers formed in this manner are between 0.1 and 500 nm, preferably between 10 and 100 nm thick depending on the method. Larger layer thicknesses of the metal layer as well as of the oxide layer can in principle be realised in practice but do not exhibit any additional advantageous effects.

In a preferred embodiment the detection element of the analytical test element according to the invention contains all reagents required for the detection reaction of the target analyte in the sample and optionally auxiliary substances. The detection element can also only contain parts of the reagents or auxiliary substances. Such reagents and auxiliary agents are well-known to an expert familiar with the technology of analytical test elements or diagnostic test carriers. For analytes that are detected enzymatically, the detection element can for example contain enzymes, enzyme substrates, indicators, buffer salts, inert fillers etc. The detection element can be composed of one or several layers and optionally contain an inert carrier, preferably on the side of the detection element that is not contacted with the sample. In the particularly preferred case that the detection reaction leads to an observable change in colour which in this connection is understood as either a change of colour, formation of a colour or disappearance of colour, it must be ensured by suitable measures that the carrier allows a visual or optical observation of the detection reaction. For this purpose the carrier material of the detection element can itself be transparent for example a transparent plastic foil such as a polycarbonate foil or have a transparent recess on the detection side. In addition to detection reactions that lead to colour changes, other detection principles are also known to a person skilled in the art which can be realised with the described test element such as electrochemical sensors.

It is necessary for the detection element that materials are used which are able to take up the liquid to be examined with the constituents contained therein. These are so-called absorbent materials such as for example fleeces, fabrics, knitted fabrics or porous plastic materials which can be used as layer materials. Suitable materials must be able to carry reagents that are required for the detection of the analyte to be determined.

Preferred materials for the detection element are papers or porous plastic materials such as membranes. Polyamide, polyvinylidene difluoride, polyethersulfone or polysulfone membranes are especially preferred as porous membrane materials. The reagents for the determination of the analyte to be detected are usually incorporated in the above-mentioned materials by impregnation.

So-called open films as described for example in EP-B-0 016 387 are especially preferably suitable for the detection element. For this solids are added as fine insoluble, organic or inorganic particles to an aqueous dispersion of film-forming organic plastics and the reagents required for the detection reaction are additionally added. Suitable film formers are preferably organic plastics such as polyvinyl esters, polyvinylacetates, polyacrylic esters, polymethacrylic acid, polyacrylamides, polyamides, polystyrene, mixed polymers such as of butadiene and styrene or of maleic acid ester and vinyl acetate or other film forming, natural and synthetic organic polymers as well as mixtures of these in the form of aqueous dispersions. The dispersions can be spread on a support to form a uniform layer which results in a water-resistant film after drying. The dry films have a thickness of 10 $\mu$m to 500 $\mu$m, preferably of 30 to 200 $\mu$m. The film can be used together with the support as a carrier or be applied to another carrier for the detection reaction. Although the reagents required for the detection reaction are normally added to the dispersion used to produce the open films, it may also be advantageous to impregnate the film that is formed with reagents after its manufacture. It is also possible to pre-impregnate the filling materials with the reagents. A person skilled in the art knows which reagents can be used to determine a particular analyte. This does not need to be elucidated in more detail here.

In addition the detection element can be provided with components which allow exclusion of interfering sample components from the detection reaction and thus act as filters for example for particulate sample components such as blood cells. For example when analysing blood samples the red blood pigment haemoglobin which is present in the red blood corpuscles (erythrocytes) can interfere with visual or optical detection methods. It is expedient to separate these interfering components from the sample, for example whole blood, before the actual detection reaction. This can be achieved by sample preparation before applying the sample to the test element such as by centrifuging whole blood and subsequently isolating the serum or plasma. It is more convenient and also simpler for a layman if the test element itself carries out this separation step by means of a suitable construction. A person skilled in the art knows means from test strip technology which ensure a reliable exclusion of erythrocytes. Examples are the use of semipermeable membranes or glass fibre fleeces to separate red blood corpuscles as known for example from EP-B-0 045 476.

It has proven to be particularly preferable for the test element according to the invention to use a detection element composed of two film layers on a transparent foil. It is important that the first layer that lies on the transparent foil scatters light considerably less than the overlying second layer. Such detection elements are for example known from the German Patent Application No. P 196 29 656.0.

Whereas the first layer contains a swelling agent such as for example methyl-vinyl-ether-maleic acid copolymer and optionally a weakly light-scattering filling material, the second layer requires a swelling agent and in any case at least one strongly light-scattering pigment and can additionally also contain non-porous filling materials as well as porous filling materials such as kieselguhr in small amounts without becoming permeable for erythrocytes.

Since the weakly light-scattering filling materials and the strongly light-scattering pigments are essentially responsible for the optical properties of the film layers, the first and the second film layer have different filling materials and pigments. The first film layer should either contain no filling materials or filling materials which have a refractive index that is close to the refractive index of water for example silicon dioxide, silicates and aluminium silicates. The average particle size of particularly preferred filler particles is about 0.06 $\mu$m. The second layer should expediently scatter light very strongly. Ideally the refractive index of the pigments in the second film layer is at least 2.5. Hence titanium dioxide is preferably used. Particles with an average diameter of about 0.2 to 0.8 $\mu$m have proven to be particularly advantageous.

Furthermore it has turned out to be preferable that the channel capable of capillary transport is additionally formed by a cover, in addition to the inert carrier and the detection element, which is preferably adjacent to the detection element and, like this, is on the side of the channel opposite to the carrier. The properties of the cover such as the material and coating can be similar to or identical to those of the carrier. A section of it replaces the detection element, preferably on the side of the capillary transport path facing the sample application opening. Since this usually contains valuable reagents such as enzymes and due to its often very complex structure is many times more expensive to manufacture than materials that are suitable for the cover, this measure considerably reduces the material and production costs. This applies especially to long capillary transport paths which are understood as paths of more than 5 mm. Moreover this measure can accelerate sample transport from the sample application opening in the test element to the detection site in the detection element in test elements in which the detection reaction is detected in a spatially exactly defined area in the detection element for example in the case of optical detection in an instrument or where it is intended to separate the sample application zone and the detection zone for example for reasons of instrument hygiene so that the transport of the sample in the capillary channel from the sample application zone to the detection area is so rapid that it does not limit the time to analyse a sample. In addition such an arrangement achieves a more convenient operation for the user.

The cover and detection element must be assembled such that both abut against each other in the final test element so that the liquid transport is not interrupted in the capillary at their site of contact by for example an unfavourable change of the capillary cross-section which is also understood to also include an interruption of a continuous boundary surface of the capillary. The dimensions of the detection element and cover must be mutually matched for this purpose. If it is not possible to assemble the two components adequately close together, the capillary contact can be achieved by subsequent sealing.

It was surprisingly found that for an especially preferred embodiment of the test carrier according to the invention, a flexible inert foil can be mounted on the side of the cover that faces the channel capable of capillary liquid transport which extends over the entire length of the cover, covers the entire width of the capillary channel and is at least partially enclosed between the opposing surfaces of the cover and detection element so that the capillary transport of liquid does not break down at the site of contact between the detection element and cover. The material and optionally the hydrophilizing coating of the foil can essentially correspond to those described above for the carrier and cover. In this quite especially preferred variant the detection element and cover are mounted as close together as possible.

A preferred embodiment of the test element according to the invention can additionally contain an intermediate layer between the carrier on one side of the capillary channel and the detection element and optionally the cover on the opposite side which like the aforementioned components is involved in the formation of the capillary active channel. The length of the intermediate layer in the direction of capillary transport corresponds especially preferably at least to the length of the channel. The intermediate layer is expediently designed such that it determines the width and optionally the height of the channel capable of capillary-active transport. The intermediate layer preferably has a recess, for example a punched hole, which corresponds to the width and height dimensions of a capillary-active channel. The length of the recess is particularly preferably slightly larger than the length of the capillary-active channel in order to thus create a vent opening. In principle the intermediate layer can be manufactured from the same materials and optionally with the same coatings which make up the carrier and/or cover. However, it has proven to be particularly preferable to manufacture the intermediate layer from a double-sided adhesive tape or strip since the intermediate layer can then also have the function of joining together the carrier and detection element and optionally the cover. This bonding can also be achieved in other ways for example by welding, heat-sealing for example with polyethylene, gluing with cold-setting adhesive or hot-melt adhesive, or clips.

In addition to the already mentioned advantages of the test element according to the invention it also has other merits. The spatial separation of the sample application site and signal detection in conjunction with the sample volume dosing enables the sample material to be handled hygienically. Especially in the case of optical detections for example with the aid of a reflection photometer, contamination of the instrument is largely ruled out since the sample can for example be applied to a test element which protrudes from the instrument whereby the amount of sample required to determine the analyte is sucked into the capillary channel and automatically transported without further measures to the detection zone of the test element located inside the instrument.

Furthermore the test element according to the invention requires considerably less sample material than conventional test elements in a quite especially preferred embodiment. Whereas the latter often require more than 12 $\mu$l sample liquid, the required minimum sample volume for the test element according to the invention is reduced to considerably less than 10 $\mu$l, preferably less than 5 $\mu$l and particularly preferably 3 to 4 $\mu$l sample. This is achieved by optimization of the sample flow exactly to the site of determination as well as by the defined layer thickness of the sample material under the detection zone. Especially in the case that the sample is blood, this can simplify sample collection for the person being examined and above all be associated with less pain.

A further subject matter of the invention is the use of an analytical test element according to the invention for the determination of an analyte in a liquid.

In addition the invention concerns a method for the determination of an analyte in a liquid sample, in particular a body fluid such as blood, plasma, serum, urine, saliva, sweat, with the aid of an analytical test element according to the invention. In this process the liquid sample is firstly contacted with the test element at the edge of the sample application opening which is interrupted by the notch. The sample liquid is transported by capillary forces into the channel that is capable of capillary liquid transport. In this process the sample wets the surface of the detection element that faces the channel and penetrates into the detection element. Optionally an analyte-specific detection reaction occurs between the sample and the reagents contained in the detection element which can be observed visually or optically by apparative means preferably by reflection photometry thus enabling conclusions to be drawn about the presence and optionally the amount of the analyte to be determined.

BRIEF DESCRIPTION OF THE DRAWINGS

The invention is elucidated in more detail by FIGS. 1 to 6 and by the following examples.

FIG. 1 shows a particularly preferred embodiment of the test element according to the invention. A schematic top view of the test element according to the invention is shown in FIG. 1A, FIGS. 1B to 1F each show cross-sectional views along the lines A–A', B–B', C–C', D–D' and E–E' respectively.

FIG. 2 shows another particularly preferred embodiment of the test element according to the invention. A schematic top view of the test element according to the invention is shown in FIG. 2A. FIGS. 2B to 2F each show cross-sectional views along the lines A–A', B–B', C–C', D–D' and E–E' respectively.

FIG. 3 also shows a particularly preferred embodiment of the test carrier according to the invention. A top view of the test element is shown in FIG. 3A. FIGS. 3B to 3F each show cross-sectional views along the axes A–A', B–B', C–C', D–D' and E–E' respectively.

FIG. 4 also shows another particularly preferred embodiment of the test carrier according to the invention. A schematic top view of the test element is shown in FIG. 4A. FIGS. 4B to 4D each show cross-sectional views along the lines C–C', D–D' and E–E' respectively.

FIG. 5 shows a particularly preferred embodiment of the test element according to the invention. A schematic top view of the test element according to the invention is shown in FIG. 5A. FIGS. 5B to 5G each show cross-sectional views along the lines A–A' (5B), B–B' (5C), C–C' (5D and 5G), D–D' (5E) and E–E' (5F) respectively.

DETAILED DESCRIPTION OF THE INVENTION

Figure 6:
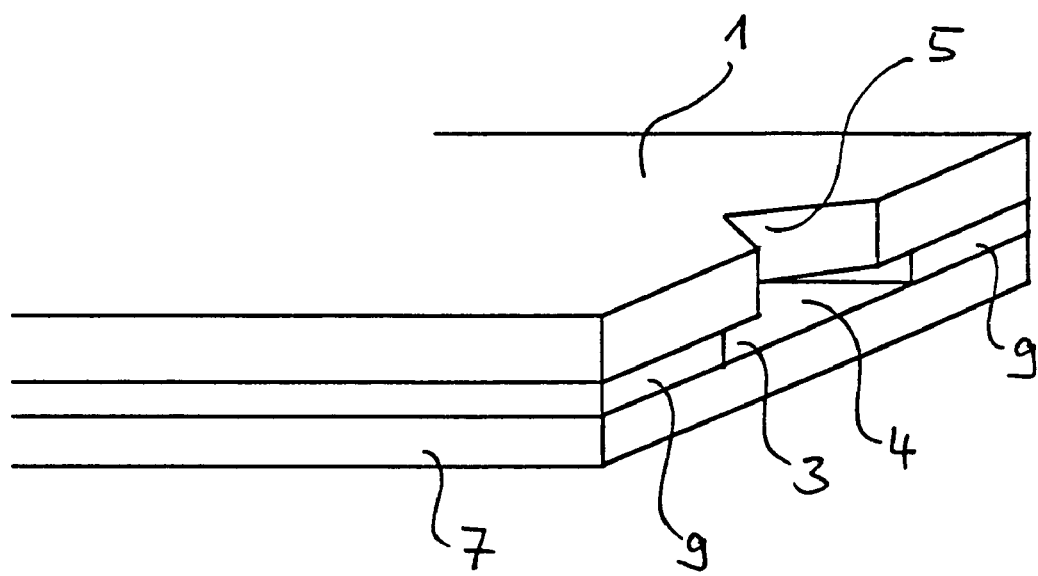
FIG. 6 shows a perspective enlargement of details of the sample application zone of the test carrier according to the invention.

The numbers in the Figures denote:
1 carrier
2 detection element
3 capillary channel
4 sample application opening
5 notch for sample application
6 vent opening
7 cover
8 gap cover foil
9 intermediate layer
10 support foil Various views (FIGS. 1A to 1F) of a particularly preferred embodiment of the test element according to the invention are shown schematically in FIG. 1. The views shown are intended to give a three-dimensional impression of the test element according to the invention. The test element is composed of a carrier (1) which is shaped such that the area which is covered by the detection element (2) forms a capillary channel (3) together with this detection element. For example a depression can be stamped or milled into the carrier. In the embodiment shown, a notch (5) is provided in the carrier (1) on the sample application opening (4) of the test element which enables the liquid drop to be directly contacted with the capillary active zone (3) when the sample is applied. A vent opening (6) is located on the side of the capillary channel (3) that is opposite to the sample application opening (4) which allows air to escape when the capillary channel is filled with sample liquid.

The capillary zone (3) extends from the sample application opening (4) to the opposite end of the detection element (2) and thus ensures a homogeneous sample distribution over the detection element (2). The sample application opening (4) and vent opening (6) limit the capillary active region (3) in the direction of capillary transport.

When using the test element shown, the sample application opening (4) of the test element is for example contacted with a blood drop located on a fingertip. In this process the blood drop comes into contact with the exposed surface which is optionally hydrophilized and simultaneously with the capillary channel (3) through the notch (5) in the carrier (1). The capillary channel fills itself with sample until it is filled from the sample application opening (4) to the vent opening (6). Afterwards the test carrier is removed from the patient's finger which ensures that only the sample that is present in the capillary channel (3) is available for the detection element (2).

A further particularly preferred embodiment is shown in FIG. 2 as an alternative to the test element shown in FIG. 1. The partial views FIGS. 2A to 2F are intended to also give a spatial impression of the test element according to the invention. The test element shown contains a channel (3) capable of capillary liquid transport which is formed by an inert carrier (1), the detection element (2) and a cover (7). The cover (7) and the detection element (2) are mounted end to end in such a way that the capillary channel (3) extends without interruption from the sample application opening (4) to the vent opening (6). The test element shown also contains a notch (5) which facilitates penetration of the sample liquid into the capillary channel.

FIG. 3 shows schematically on the basis of various views (FIGS. 3A to 3F) how use of a gap cover foil (8) can reliably prevent the capillary active zone (3) from breaking down at the contact site between the detection element (2) and cover (7). The gap cover foil (8) can additionally be provided with a hydrophilic surface on the side facing the capillary channel (3) which facilitates the capillary transport of a liquid drop from the sample application opening (4) to the vent opening (6). Such a hydrophilization in the area of the notch (5) in the carrier (1) is particularly advantageous since it accelerates the penetration of the sample material into the capillary channel.

In contrast to the particularly preferred embodiments of the test carrier according to the invention shown in FIGS. 1 to 3, the geometry of the capillary channel (3) in the test element shown in FIG. 4, which is also a particularly preferred embodiment of the subject matter of the invention, is not determined by the shape of the carrier (1) but rather primarily by an intermediate layer (9). FIGS. 4A to 4D are in turn intended to give a three-dimensional impression of the test carrier construction. The intermediate layer (9) can be made of a double-sided adhesive tape which, apart from determining the capillary channel geometry, also serves to bond the other components that are involved in forming the capillary active zone (3) i.e. the carrier (1), cover (7) and detection element (2). The cover (7) and the detection element (2) in the test element shown are again mounted to closely end to end that the capillary channel (3) extends without interruption from the notch (5) at the sample application opening (4) to the vent opening (6).

The test element shown in various views in FIGS. 5A to 5F is a very specially preferred embodiment of the subject matter of the invention. It combines all components and thus other advantages of the test elements which are shown in FIGS. 1 to 4.

An intermediate layer (9) is mounted on a carrier (1) in the form of a double-sided adhesive tape. In the area of the capillary channel (3) the intermediate layer (9) has a recess which determines the length and width of the channel (3). Its height is given by the thickness of the intermediate layer (9). On the side of the capillary channel (3) which is opposite to the carrier (1), a cover (7) is located adjacent to the detection element (3). A gap cover foil (8) is provided to ensure capillary continuity. This can be hydrophilized to enable a rapid transport of sample from the sample application opening (4) to the vent opening (6) which marks the opposite end of the capillary channel. An additional advantage of the hydrophilization is that a drop of sample liquid can be applied directly to a hydrophilic surface in the area of the notch (5) which is surrounded on several boundary sides by the capillary active zone (3). This leads to a rapid penetration of the liquid drop into the test element.

FIG. 5G shows how the intermediate layer (9) can be covered by a protective foil (10) in order to cover exposed areas of the adhesive tape. However, in this case the vent opening (6) must not be covered.

Finally a detail enlargement of a perspective view of the sample application area of a particularly preferred embodiment of the test element according to the invention is shown in FIG. 6. The notch (5) in the carrier (1) facilitates penetration of a sample liquid from the sample application opening (4) into the capillary active zone (3) which in the present case is formed by the carrier (1), intermediate layer (9) and cover (7). In addition to the shape shown the notch can also have any other desired shape which serves the purpose according to the invention.

EXAMPLE 1

Manufacture of the Analytical Test Element According to the Invention

A double-sided adhesive tape with a thickness of 100 µm is glued onto a 350 µm thick foil of polyethylene terephthalate (Melinex®, ICI, Frankfurt am Main, Germany) coated with a 30 nm thick layer of aluminium which was completely oxidized with water vapour. The foil has a length of 25 mm and is 5 mm wide. A central notch-shaped recess of 1 mm width and 2 mm length is located on one of the short sides. The adhesive tape has a punched hole of 2 mm width and more than 15 mm length which defines the dimensions of the capillary channel. The length of the punched hole is selected to be slightly larger than the desired length of the capillary-active channel which is determined by its cover in order to ensure venting of the channel during filling with sample liquid. A 3 mm long and 5 mm wide detection film is glued onto the side of the adhesive tape which provides the venting at a distance of 1 mm from the end of the punched hole. A film is used as the detection film as is known from the German Patent Application No. P 196 29 656.0. The detection film is specific for the detection of glucose. A 12 mm long and 5 mm wide cover layer is glued onto the region of the adhesive tape that is still open between the notch-shaped recess and detection film so that the cover layer and detection film abut one another. The cover layer is composed of a 150 µm thick polyethylene terephthalate foil provided on one side with adhesive onto which a 6 µm thick polyethylene terephthalate foil (both: Hostaphan®, Hoechst, Frankfurt am Main, Germany) coated with a 30 nm thick oxidized aluminium layer on the side facing the capillary channel is glued. In this case the thinner foil extends ca. 500 µm beyond the thicker foil on the side facing the detection film. When the cover layer is mounted on the adhesive tape care must be taken that the protruding end of the thinner foil comes to lie between the detection element and the thicker foil of the cover layer. In order to cover areas of the adhesive foil that are still exposed, these are covered with a 175 µm thick Melinex® foil without, however, covering functional areas.

The test element obtained in this manner has a capillary channel of 15 mm length, 2 mm width and 0.1 mm height. The channel can take up 3 µl sample liquid. An area of 3 mm×2 mm of the detection film is wetted by the sample.

EXAMPLE 2

Measurement of the Blood Glucose Concentration with the Aid of the Test Element from Example 1

A drop of sample liquid is placed on the sample application site of the test element from example 1. The capillary of the test element automatically fills with sample within 2 s. If glucose is present in the sample a colour development is visible in the detection film after a few seconds. The end point of the reaction is reached after ca. 30 to 35 s. The colour obtained can be correlated with the glucose concentration of the sample and either evaluated visually or by reflection photometry.

The invention claimed is:

1. Analytical test element comprising:
   an inert cover,
   an inert carrier having a first surface,
   a detection element being formed to permit liquid penetration therein and including at least one reagent contained in the detection element, the detection element including a second surface facing the first surface, and
   a capillary channel including a sample opening and a vent opening and extends in a direction of capillary transport from the sample opening to at least an edge of the detection element that is nearest to the vent opening, wherein the capillary channel is formed by the inert carrier, the detection element, and the inert cover, the cover and the detection element being mounted end to end in such a way that the capillary channel extends without interruption from the sample application opening to the vent opening and a notch is positioned at an edge of the test element forming the sample opening so that a surface opposite to the notch is exposed.

2. The analytical test element as claimed in claim 1, wherein at least one of the surfaces forming an inner surface of the channel is hydrophilized.

3. The analytical test element as claimed in claim 2, wherein the exposed surface opposite to the notch is hydrophilized.

4. The analytical test element as claimed in claim 2 wherein a layer of oxidized aluminium is used for the hydrophilization.

5. The analytical test element as claimed in claim 2, wherein the hydrophilization is achieved by a hydrophilic material.

6. The analytical test element as claimed in claim 2, wherein the hydrophilization is achieved by a hydrophilic layer.

7. The analytical test element as claimed in claim 1, wherein the detection element is a filter for particulate sample components.

8. The analytical test element as claimed in claim 1, wherein the channel is at least partially formed by the carrier, the cover and the detection element wherein the cover and detection element are arranged adjacent to one another in such a way that the cover is located on the side facing the sample application opening.

9. The analytical test element as claimed in claim 8, wherein a flexible inert foil is mounted on the side of the cover that faces the channel which extends over the entire length of the cover, covers the entire width of the capillary channel and is at least partially enclosed between the opposing surfaces of the cover and detection element so that the capillary liquid transport does not break down at the site of contact between the detection element and cover.

10. Method of detecting the presence of an analyte in a liquid with an analytical test element as claimed in claim 1, wherein
   the test element is contacted with the liquid sample at the edge of the sample application opening, which is interrupted by the notch so that the sample is transported by capillary forces into the channel and wets and penetrates the surface of the detection element specific for the detection of the analyte that faces the channel, and the liquid sample in the detection element is observed to determine whether optical changes in the detection element exist, wherein the changes relate to a presence of the analyte in the liquid sample.

11. The analytical test element as claimed in claim 1, wherein an intermediate layer is present between the carrier and detection element.

12. The analytical test element as claimed in claim 11, wherein the intermediate layer is formed to bond the carrier and detection element.

13. The analytical test element as claimed in claim 12, wherein the intermediate layer is formed to bond the cover and the carrier.

14. The test element of claim 1 further comprising a cover defining a portion of the channel and wherein the detection element and the sample application opening are non-contiguous.

15. An analytical test apparatus comprising:
an inert cover,
an inert carrier having a first surface, and
a detection element being formed to permit liquid penetration therein and including at least one reagent contained in the detection element, the detection element having a second surface facing the first surface, the channel including a sample opening and a vent opening and extends in a direction of capillary transport from the sample opening to at least an edge of the detection element that is nearest to the vent opening, wherein the capillary channel is formed by the inert carrier, the detection element, and the inert cover, the cover and the detection element being mounted end to end in such a way that the capillary channel extends without interruption from the sample application opening to the vent opening and a notch is positioned at an edge of the test element forming the sample opening so that one side of the edge is discontinuous.

16. The apparatus of claim 15, wherein at least one of the surfaces forming the channel is hydrophilized.

17. The apparatus of claim 16, wherein the hydrophilization is achieved by a hydrophilic material.

18. The apparatus of claim 16, wherein the hydrophilization is achieved by a hydrophilic layer.

19. The apparatus of claim 18, wherein a layer of oxidized aluminium is used for the hydrophilization.

20. The apparatus of claim 15, wherein the surface opposite to the notch is hydrophilized.

21. The apparatus of claim 15, further comprising an inert cover cooperating with the carrier and the detection element to define at least a portion of the channel.

22. The apparatus of claim 21, wherein the cover and the detection element are located on the side of the channel that is opposite the carrier.

23. The apparatus of claim 21, wherein the cover and detection element are arranged adjacent to one another so that the cover is positioned on the side facing the sample application opening.

24. The apparatus of claim 21, wherein the detection element and the cover abut each other.

25. The apparatus of claim 21, further comprising a flexible inert foil mounted on the cover and facing the channel.

26. The apparatus of claim 25, wherein the foil covers the entire width of the channel and is at least partially enclosed between the opposing surfaces of the cover and the detection element.

27. The test element of claim 15 further comprising a cover defining a portion of the channel and wherein the detection element and the sample application opening are non-contiguous.

28. A method for determining an analyte in a liquid sample, the method comprising the steps of:
providing an analytical test element including an inert cover, an inert carrier having a first surface, a detection element being formed to permit liquid penetration therein and including at least one reagent contained in the detection element, the detection element including a second surface facing the first surface, and a capillary channel including a sample opening and a vent opening and extends in a direction of capillary transport from the sample opening to at least an edge of the detection element that is nearest to the vent opening, wherein the capillary channel is formed by the inert carrier, the detection element, and the inert cover, the cover and the detection element being mounted end to end in such a way that the capillary channel extends without interruption from the sample application opening to the vent opening and a notch is positioned at an edge of the test element forming the sample opening so that a surface opposite to the notch is exposed,
contacting the test element with the liquid sample at the notch so that the liquid sample is transported by capillary forces into the channel, and
observing the liquid sample in the detection element to determine whether optical changes in the detection element exist following contact with the liquid sample, wherein the changes relate to a presence of the analyte in the liquid sample.

29. The method of claim 28, further comprising the steps of providing at least one reagent in the detection element and conducting an analyte-specific detection reaction with the at least one reagent.

30. The method of claim 29, wherein the observing step includes visual observation.

31. The method of claim 29, wherein the observing step includes optical observation.

32. The method of claim 29, wherein the observing step includes the step of conducting a reflection photometric measurement.

* * * * *